(12) United States Patent
Petit et al.

(10) Patent No.: US 9,186,195 B2
(45) Date of Patent: Nov. 17, 2015

(54) BENDING MACHINE WITH A CAM FOR AN ORTHOPAEDIC ROD

(71) Applicant: Safe Orthopaedics, Eragny sur Oise (FR)

(72) Inventors: Dominique Petit, Verton (FR); Jean Charles Le Huec, Pessac (FR)

(73) Assignee: SAFE ORTHOPAEDIC, Eragny sur Oise (FR)

( * ) Notice: Subject to any disclaimer, the term of this patent is extended or adjusted under 35 U.S.C. 154(b) by 0 days.

(21) Appl. No.: 14/389,832

(22) PCT Filed: Apr. 2, 2013

(86) PCT No.: PCT/FR2013/050721
§ 371 (c)(1),
(2) Date: Oct. 1, 2014

(87) PCT Pub. No.: WO2013/150233
PCT Pub. Date: Oct. 10, 2013

(65) Prior Publication Data
US 2015/0047410 A1 Feb. 19, 2015

(30) Foreign Application Priority Data

Apr. 2, 2012 (FR) .................................. 12 52995

(51) Int. Cl.
*B21D 7/06* (2006.01)
*A61B 17/88* (2006.01)
*B21D 7/022* (2006.01)
*A61B 17/70* (2006.01)

(52) U.S. Cl.
CPC ............ *A61B 17/8863* (2013.01); *B21D 7/022* (2013.01); *B21D 7/063* (2013.01); *A61B 17/7002* (2013.01)

(58) Field of Classification Search
CPC .... B21D 7/022; B21D 7/063; A61B 17/7002; A61B 17/8863
USPC ............................................. 72/409.1, 409.11
See application file for complete search history.

(56) References Cited

U.S. PATENT DOCUMENTS

| | | | |
|---|---|---|---|
| 3,824,834 A | 7/1974 | Durham | |
| 4,389,872 A | 6/1983 | Kowal | |
| 4,474,046 A | 10/1984 | Cook | |
| 5,490,409 A | 2/1996 | Weber | |
| 5,819,580 A | 10/1998 | Gauthier | |
| 6,006,581 A * | 12/1999 | Holmes | 72/458 |
| 8,491,601 B2 * | 7/2013 | Schmuck et al. | 606/101 |
| 8,770,006 B2 * | 7/2014 | Harper | 72/409.01 |
| 2009/0254326 A1 | 10/2009 | Isaacs | |

FOREIGN PATENT DOCUMENTS

FR 1342386 A 11/1963

* cited by examiner

*Primary Examiner* — David B Jones
(74) *Attorney, Agent, or Firm* — Bachman & LaPointe, P.C.

(57) ABSTRACT

A bending machine with a cam made up of two articulated arms, comprising a main roller that is coaxial with the axis of articulation of the arms, the end of the short portion of each one of the arms having means for exerting a bending force on a rod, wherein the means are made up of eyelets, each one of the eyelets being mounted on the end of the short portion of one of the arms in a rotatably mobile manner about an axis parallel to the axis of the main roller.

18 Claims, 6 Drawing Sheets

BENDING MACHINE WITH A CAM FOR AN ORTHOPAEDIC ROD

BACKGROUND

The present invention relates to the field of tools for manual bending of rods, in particular for bending orthopaedic rods such as intervertebral linking elements.

The rods are typically steel or titanium rods, with a cross-section of five to six millimeters. The sought bending radii are usually comprised between twenty and one hundred millimeters. Bending requires the application of a very large force of several thousand Newtons, in particular for titanium rods.

A plurality of patents are known in the prior art that describe manual bending tools made up of two articulated arms supporting a main roller and two secondary rollers each mounted on the end of one of the two arms. Such tools are described in American patents U.S. Pat. No. 4,474,046, U.S. Pat. No. 5,490,409 and U.S. Pat. No. 5,819,580.

The patents propose the use of an adjustable main roller to optimize the bending angle of the rod.

The manual bending tools have a plurality of disadvantages.

First of all, the known implementation of bending tools involves considerable physical exercise, which is incompatible with careful, accurate manipulation: the operator must exercise a force to the limit of his or her own strength on the arms, and this obliges the operator to focus all of his or her attention on exercising this force, rather than on the precise positioning of the rod to be bent and on the permanent verification that a correct positioned is maintained. When the force is relaxed, the rod exits the head of the tool and falls. This is especially problematic in the case of orthopaedic rods that necessarily require that sterility is maintained.

A second problem relates to the limits of the bending angle. The tools of the prior art do not allow bending with very small radii of curvature, and are generally limited to radii of curvature of more than around fifty millimeters.

A third problem is that of the weight and the cleaning of said tools. In order to withstand the considerable forces applied by the user, these tools generally have solid metal arms, and articulations that have areas where dirt may accumulate.

SUMMARY

In order to solve said problems, the invention relates, according to the broadest interpretation thereof, to a bending machine with a cam made up of two articulated arms, comprising a main roller that is coaxial with the axis of articulation of said arms, the end of each one of said arms comprising means for exerting a bending force on a rod, wherein said means are made up of closed eyelets, each one of said eyelets being mounted on the end of the short portion of one of said arms so as to be rotatable about an axis that is parallel to the axis of said main roller.

The "short portion" of the arm is understood to be the portion that extends in front of the point of articulation. The point of articulation is located between a short portion supporting the eyelets and a long portion which is used to exert a force, forming a force-amplifying lever.

Advantageously, each eyelet comprises an opening with an axis perpendicular to the axis of rotation of the eyelet, the opening being arranged such as to allow the passage of the rod to be bent.

According to a specific embodiment, each eyelet is made up of a cylindrical portion provided at the end with a head having an opening passing through same, said part being mounted freely rotatable through a bore made in the end of the short portion (5, 6) of said arms. Thus configured, the eyelets provide axial guiding of the rod throughout the bending operation, enabling considerable, uniform bending of the rod.

The two arms are preferably vertically adjacent.

Advantageously, the eyelet mounted on the lower arm has a base with a thickness matching the thickness of the upper arm, so that the centers of the openings of the two eyelets are coplanar.

According to another advantageous embodiment, the two arms are flat, and are arranged parallel to the median plane.

Preferably, the angle formed between the straight line passing between the axis of rotation of one of the eyelets and the axis of rotation of the main roller, and the axis passing between the axis of rotation of a main roller and the gripping area of the corresponding arm is comprised between 75° and 100°, preferably around 90°

Advantageously, the portion of the arm opposite the eyelet forms a divergent angle, in other words, the rear segment of the arm is not aligned with the main segment of the handle, but rather is deflected towards the outside.

According to one alternative embodiment, the main roller has a groove with a radius substantially equal to that of the rod to be bent, the center of which is coplanar with the center of the openings formed in the eyelets.

According to a preferred embodiment, the arms are configured such as to allow the crossing of the intermediate areas thereof.

According to a specific embodiment, the arms are made of a preferably sterile polymer for the production of a disposable tool.

According to one alternative embodiment, each head supports at the transverse end thereof crossed by the axis of rotation of the eyelet a vertical extension, which is coaxial with said axis of rotation, with a height matching the thickness of the head of the complementary arm, said head also including a radial extension, extending parallel to the triangular area, between the axis of rotation of the eyelet and the axis of rotation of the main roller such as to form a fork suitable for receiving the triangular area of the complementary head in order to form a hinge.

Advantageously, the vertical extension, the radial extension and the head are formed integrally by molding a single part.

According to one alternative, said head has a triangular shape extending towards the outside.

According to another embodiment, at least one of the handles has markings that represent the radius of curvature achieved.

BRIEF DESCRIPTION OF THE DRAWINGS

Further objectives and advantages of the invention will become apparent from the following description, made in reference to the appended drawings, relating to a non-exhaustive example of an embodiment of a bending machine according to the invention, wherein.

DETAILED DESCRIPTION

Figure 1:
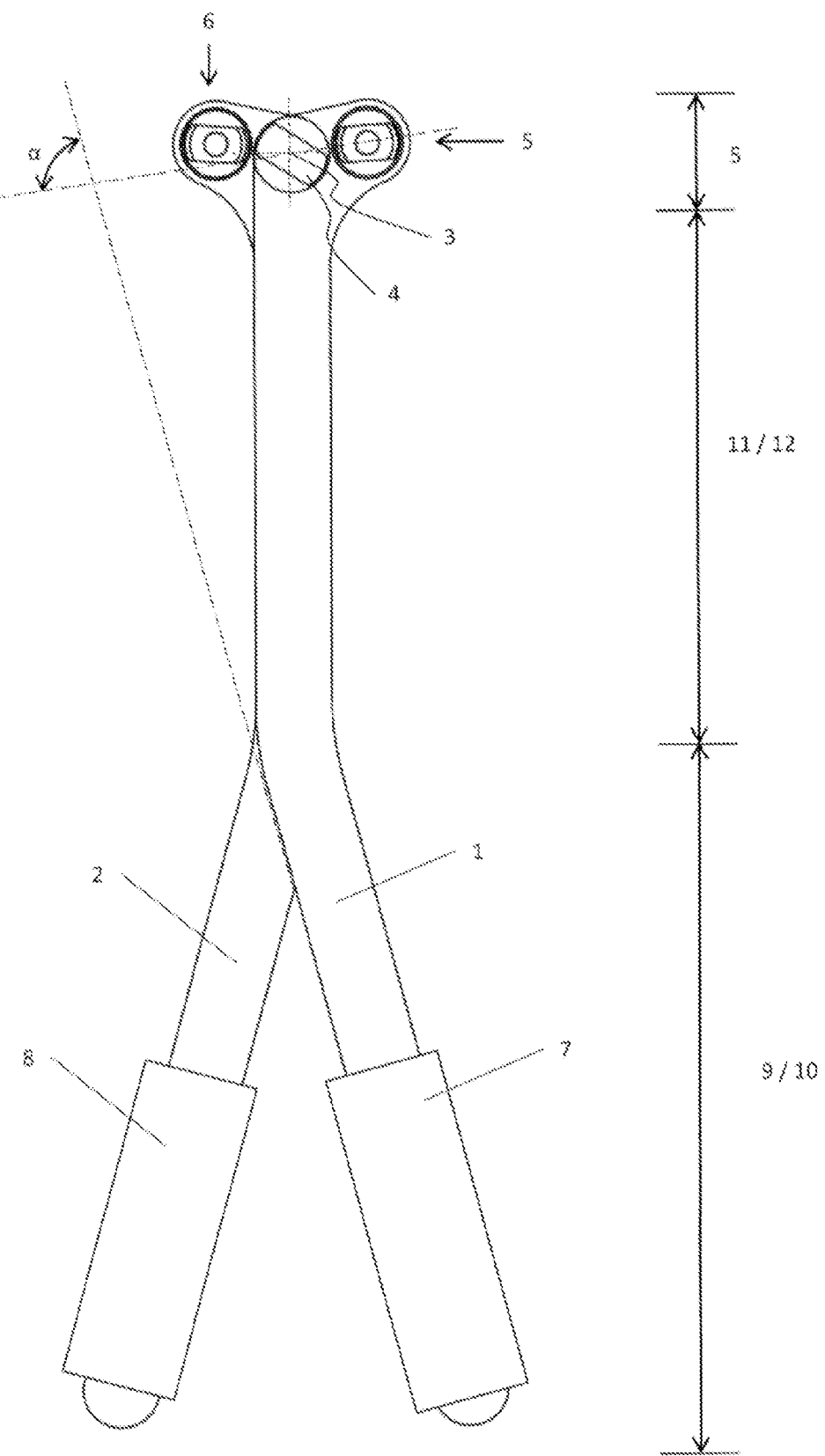
FIG. 1 is a view of a bending machine in neutral position.

FIG. 1 is a non-exhaustive example of an embodiment of a bending machine according to the invention. The machine comprises an upper arm (1) and a lower arm (2) articulated by an axis of rotation (3) also supporting a main roller (4).

Each of the arms (1, 2) is made up of a bending head (5, 6) and a handle (7, 8). The arms (1, 2) are cut from a sheet of metal with a thickness of 3 millimeters. The arms can also be made by molding a plastic material filled with carbon fiber or fiberglass. The median surfaces of the arms (1, 2) are parallel and planar such as to allow the sliding of one arm over the other, throughout the entire authorized travel thereof.

The arms have a substantially constant width, for example of sixteen millimeters, for metal arms made of steel.

The handle (7, 8) of the arms (1, 2) is sheathed at the rear portion thereof in order to make same easier to grip. The thickness of the sheathing is determined such as not to prevent the arms from being placed vertically adjacent. If necessary, the sheathing does not extend over the facing surfaces of the arms (1, 2).

The handle (7, 8) has a divergent shape, with a rear portion (9, 10) forming an angle of around 160° with the front portion (11, 12).

The length of the rear portion (9, 10) is around 150 millimeters, and the length of the front portion (11, 12) is around 100 millimeters. The length of the rear portion (9, 10) is substantially 1.5 times the length of the front portion (11, 12).

At the start of the bending operation, corresponding to the phase during which the maximum forces are exerted, the opening of the rear portion (9, 10) is around 100 millimeters, for correct gripping of the instrument. An action can thus be exerted using a single hand.

The short portions (5, 6) of the arms (1, 2) have a length of around 25 millimeters. The arms each support an eyelet (13, 14) which can rotate about an axis parallel to the axis of rotation (3) of the main roller (4).

In the shown embodiment, each eyelet (13, 14) is made up of a cylindrical part extended at one of the ends thereof by a flat head (130, 140) with a smaller cross-section than the cross-section of the part. The head (130, 140) is crossed by a diametrical opening (15, 16) with a cross-section that is slightly greater than that of the rod to be bent. For example, the cross-section of the diametrical opening (15, 16) is 6 millimeters for rods to be bent with a cross-section of 5.5 millimeters. The clearance makes it possible not only to insert the rod easily, but also to move and remove same despite the deformations applied during the bending operation. The cylindrical part is mounted through a bore made at the end of the short portion (5, 6) of the related arm (1, 2), which has an axis parallel to the axis of the main roller (4). The part has a cross-section that is slightly smaller than that of the bore such as to leave a clearance that allows the rotation of the eyelet inside the bore.

Advantageously, the opening (15, 16) of each eyelet (13, 14) is arranged such as to have an axis perpendicular to the axis of rotation of the eyelet. Given that the eyelets (13, 14) are mounted freely rotatable on the arms, the axis of the openings (15, 16) remains substantially perpendicular to the axis of the rod (19) during the centering operation. Thus, during the bending operation, the rod, under the action of the bending force applied by the main roller (4) slides axially inside the openings.

According to a specific embodiment, each eyelet (13, 14) is shaped and arranged relative to the main roller (4) in order to have, when the head (130, 140) of each eyelet is positioned such as to present the related opening (15, 16) opposite the main roller (4), a separation allowing the rod (19) to pass between the main roller (4) and the eyelets (13, 14). The outer perimeter of each head (130, 140) extending in a plane perpendicular to the axis of the openings (12, 14) thus constitutes a bearing area which enables, together with the main roller (4), the bending of the rod. Advantageously, the bearing surface of each head (130, 140) is provided with a groove having a radius substantially equal to that of the rod to be bent. According to an advantageous configuration, the outer perimeter of each eyelet has at least one planar bearing area, the remaining area being circular. Since it is provided with two different areas, the eyelet thus provides two separate bending radii of the rod. It is clearly obvious that the number of bearing areas is not limited to one or two, and that a perimeter can be provided that offers more than two separate areas according to the desired number of bending radii.

The angle formed between the straight line passing between the axis of rotation of one of the eyelets and the axis of rotation of the main roller, and the axis passing between the axis of rotation of a main roller and the gripping area of the corresponding arm is around 90°.

The main roller (3) as well as the eyelets (13, 14) are attached by means of nuts. The nuts can optionally be removed in order to enable the replacement of the eyelets, in particular to adapt to the size of the rods to be bent.

Figure 2:
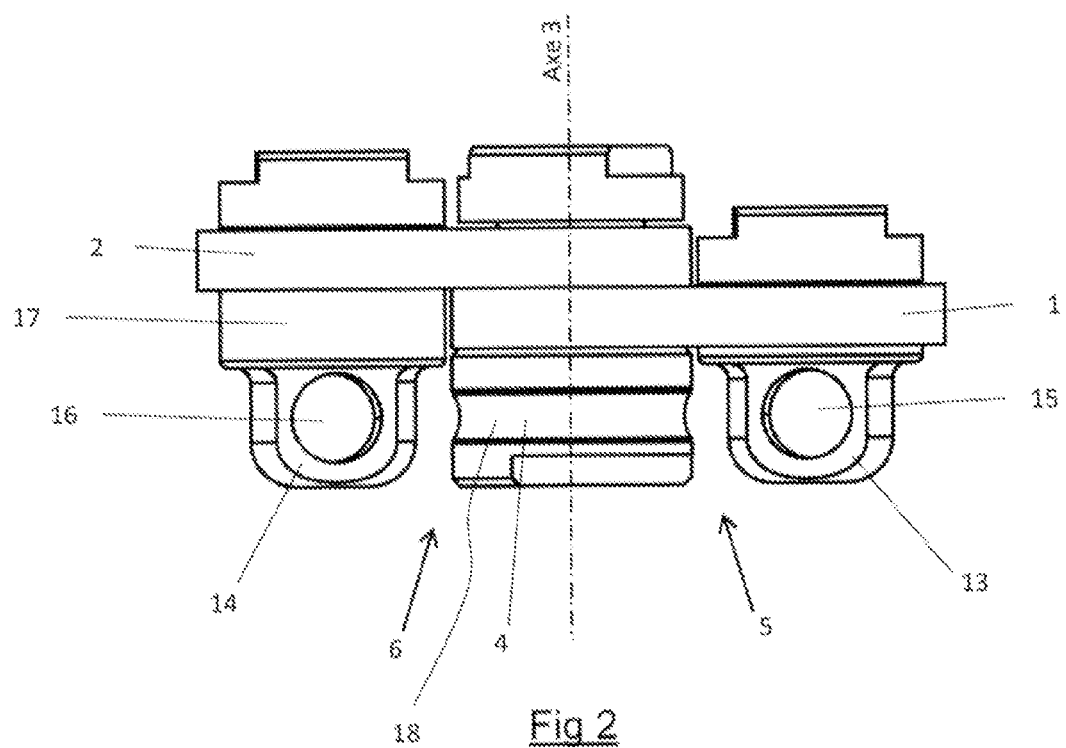
FIG. 2 is a front view of the head of the bending machine according to the invention.

As shown in FIG. 2, in order to compensate for the offset resulting from the thickness of the arms, the eyelet (14) mounted on the lower arm (2) has a base (17) with a thickness substantially equal to that of the arm (2).

The main roller (3) is optionally freely rotatable. The roller has a groove (18) in which the radius of curvature is 2.8 millimeters, substantially identical or slightly larger than that of the rod to be bent.

The distance between the axis (3) of the main roller and the axis of each one of the eyelets is minimal, limited by the cross-section of the eyelet and the main roller and, if necessary, of the base of the eyelet (17) and optionally of the nuts. In the described example, said distance is 18 millimeters.

Figure 3:
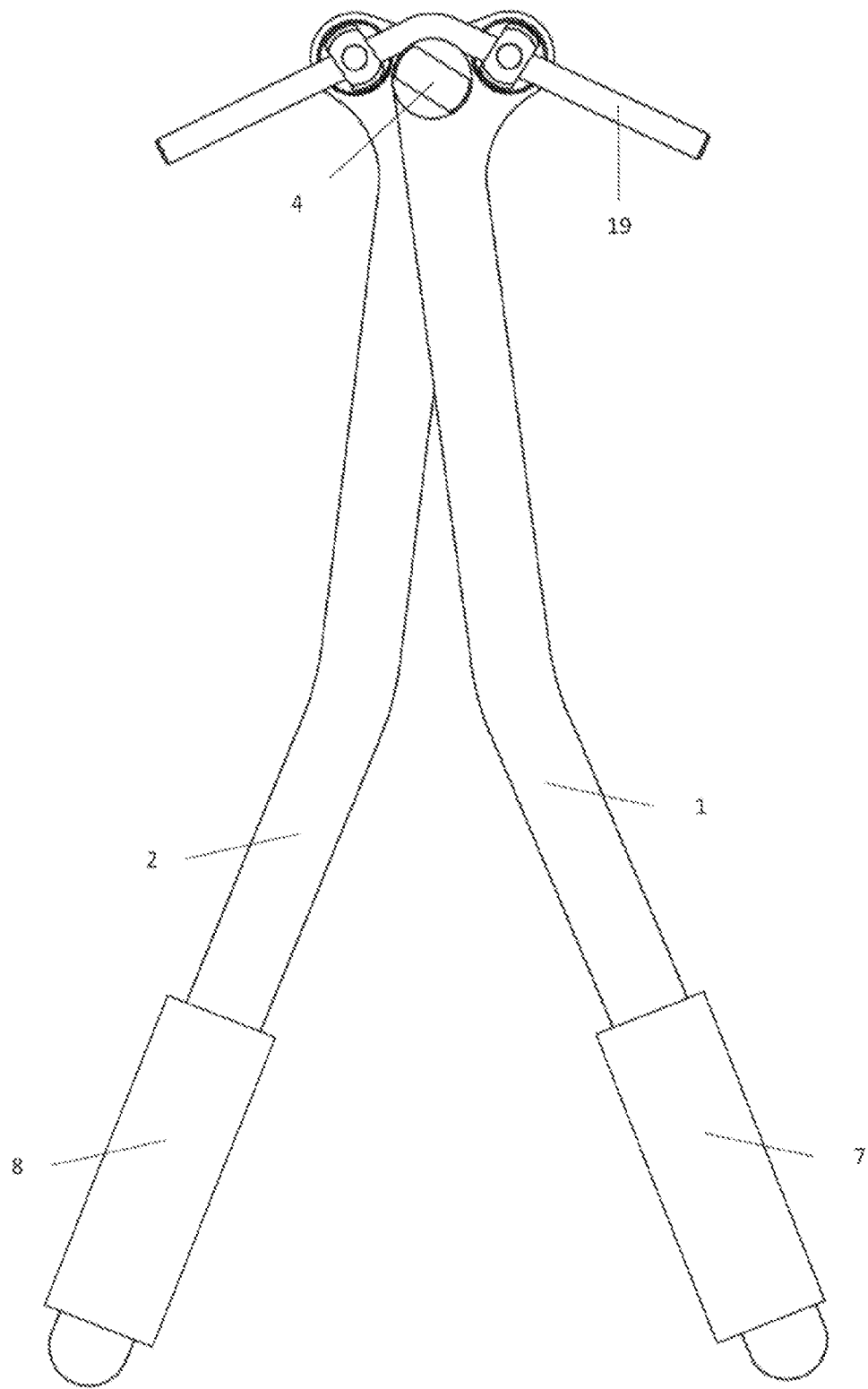
FIG. 3 is a view of said bending machine, with a rod at the start of the bending operation.

FIG. 3 shows a view of the bending machine at the start of the bending operation. The intervertebral linking rod (19) is slid into the two openings of the eyelets and slides into the groove of the main roller (4). The separation between the two arms is large enough to free up a path for the passage of the rod (19).

As of this time, the linking rod (19) is held in place, and cannot fall even if the bending machine is operated incorrectly (except in the highly unlikely situation that the tool is vertical in a configuration in which the two openings are aligned vertically and no force is exerted on the arms).

When the handles (7, 8) of the two arms (1, 2) are moved towards one another, a force is exerted via the two eyelets and the main roller, with a considerable lever effect, causing the deformation of the rod to be bent (19). In the described example, the forces are amplified by a factor of around 12.

The level of amplification is determined by the ratio between the length of the rear portion (9, 10) calculated between the point of articulation supporting the axis of rotation (3) of the main roller, and the length of the short portions (5, 6) calculated between said point of articulation supporting the axis of rotation (3) of the main roller (4) and the axis of rotation of the eyelet (13, 14) supported by the arm.

Figure 4:
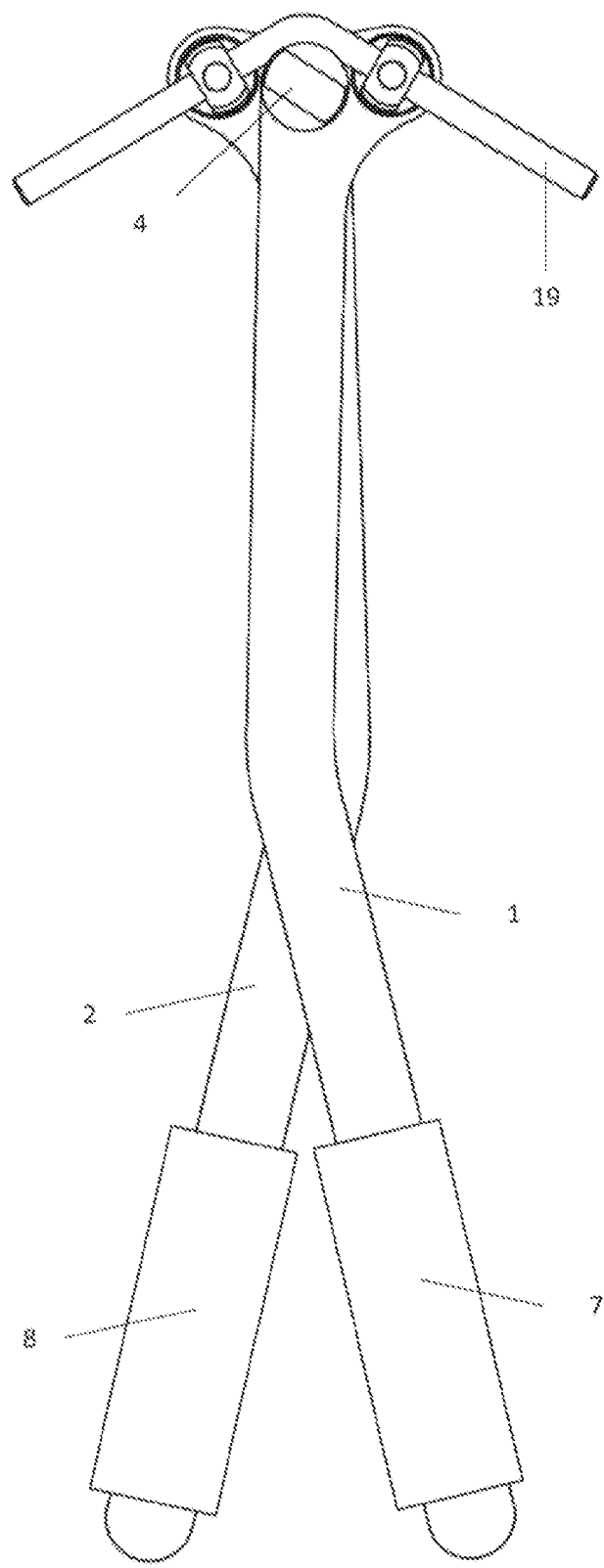
FIG. 4 is a view of said bending machine, with a rod at the end of the bending operation.

FIG. 4 shows the situation in which a particularly small radius of curvature is sought. The configuration of the handles (7, 8) allows for a considerable travel, exceeding the position in which the arms are parallel. The arms can cross, which makes it possible to increase the travel amplitude.

Figure 5:
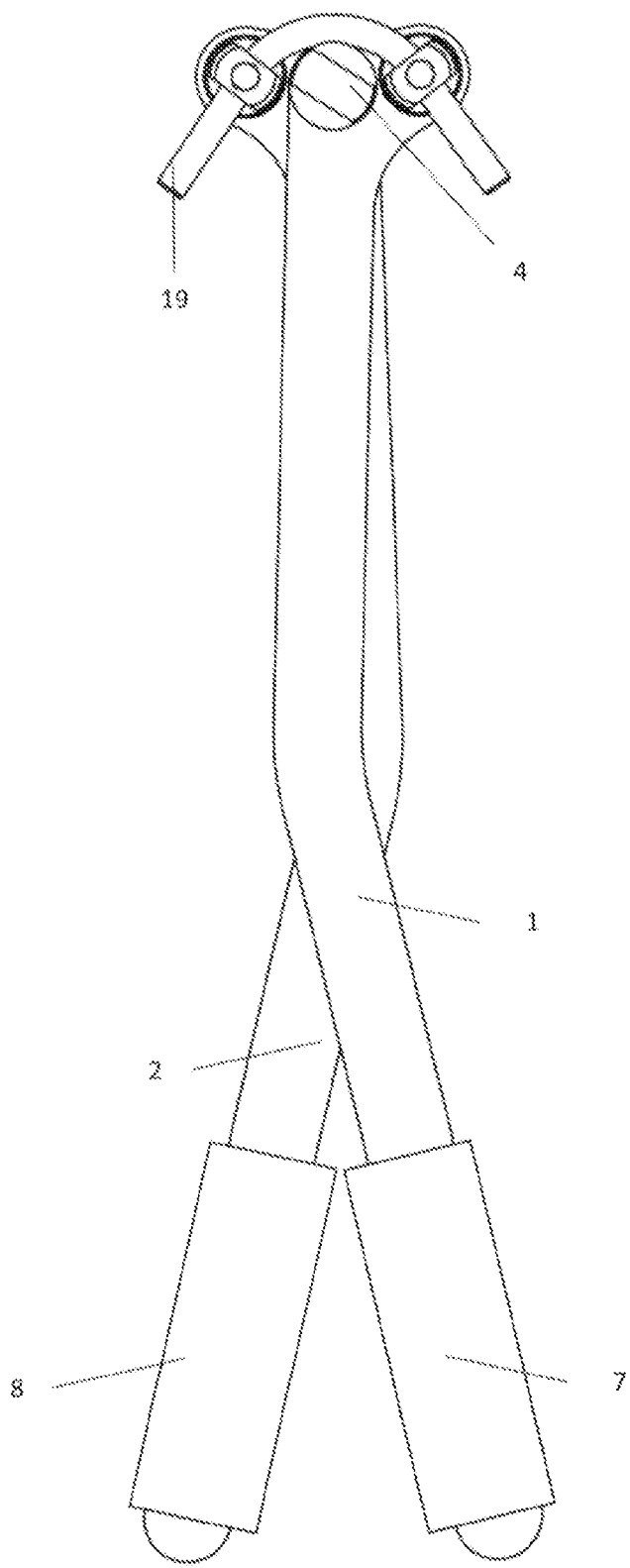
FIG. 5 is a view of said bending machine, with a rod having undergone a series of bending operations.

FIG. 5 shows the situation in which the rod (19) undergoes a series of bending operations via regular movements of the rod. A first bending operation is performed, then the rod is moved longitudinally by several millimeters relative to the eyelets and to the roller before performing a new bending step, and so on.

Figure 6:
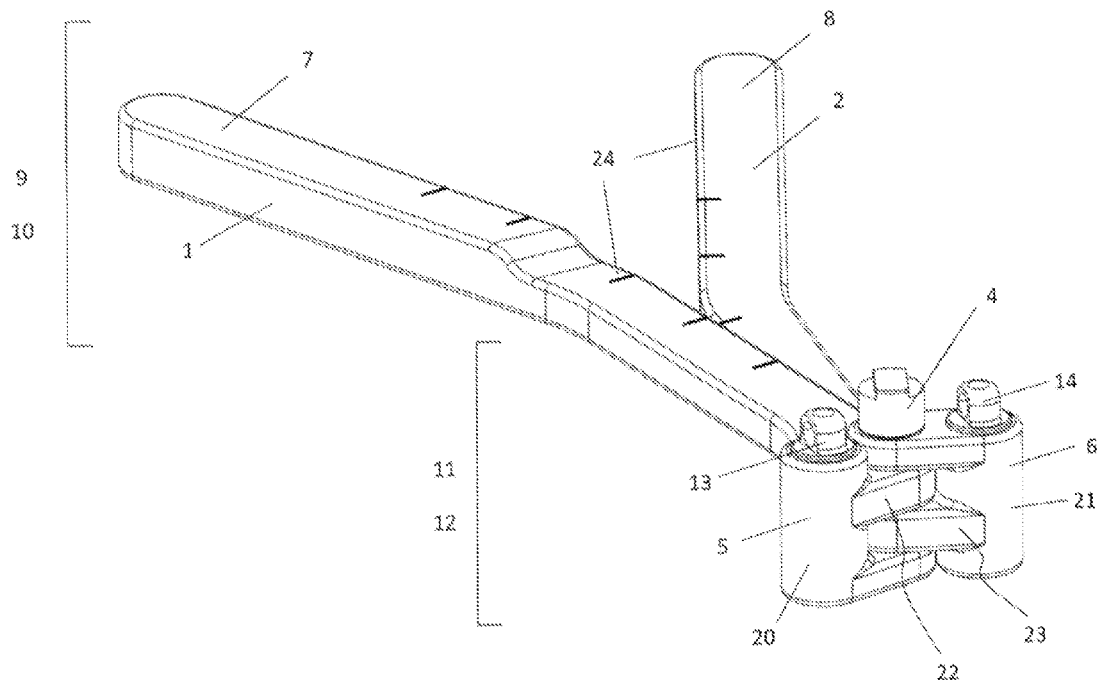
FIG. 6 is a front three-quarter view of an alternative embodiment of a bending machine according to the invention.
Figure 7:
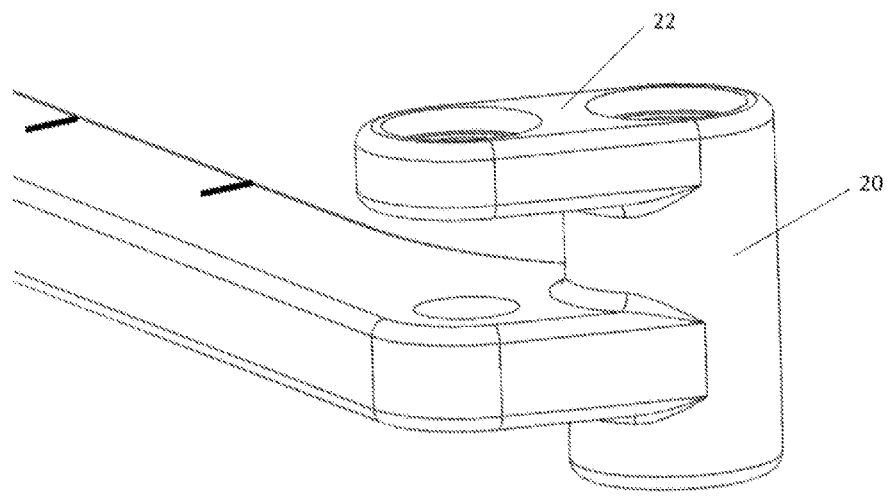
FIG. 7 is a perspective view of the head of an arm according to said alternative embodiment.

FIGS. 6 and 7 relate to an alternative embodiment of the invention, showing a front three-quarter view of a bending machine according to the invention and a perspective view of the head of an arm according to the embodiment, respectively.

In the embodiment, the arms (1, 2) are not made up of flat metal elements, but rather of molded elements with a substantially rectangular cross-section. The rectangular cross-section is determined such as to have a width (measured in a plane parallel to the median plane of the instrument) greater than the thickness thereof (measured according to an axis parallel to the axis of rotation of the main roller). The arms can be made of a filled polymer for use in disposable surgical instruments.

As in the preceding embodiment, the two arms (1, 2) are identical. The feature is not, however, necessary, and it would be possible to produce an instrument with two different, complementary arms. The feature is, however, preferred, since it reduces manufacturing costs, due to the use of the same single mould for the right arm and the left arm, and additionally results in constructions that are highly solid and reliable in mechanical terms.

Each of the arms (1, 2) has, as in the first alternative embodiment, a rear portion (9, 10) in which the rear segment forms the respective handles (7, 8). The handles (7, 8) are slightly divergent towards the outside, with an angle of around 15° relative to the front segment (11, 12), comprised between the axis of rotation (3) and the handle. The handles (7, 8) have a thickness that is greater than that of the front segment (11, 12) in order to improve the comfort of use and to strengthen the arm of the lever, which is subjected to considerable forces during bending. The thickness of the handle (7, 8) is around 15 millimeters, while the thickness of the front segment (11, 12) is 10 millimeters. The handle (7, 8) can have an ergonomic shape adapted to the hand of a user, for example in the shape of a grip with fluted recesses.

Each head (5, 6) in the example describes a triangular shape extending towards the outside. The triangular area supports at the end thereof through which the axis of rotation of the eyelet passes respectively (13, 14) a vertical extension (20, 21), coaxial with the axis of rotation, with a height matching the thickness of the head (6, 5) of the complementary arm.

The head (5, 6) also includes a radial extension (22, 23), extending parallel to the triangular area, between the axis of rotation of the eyelet (13, 14) and the axis of rotation (3) of the main roller.

The radial extension (22, 23) and the triangular area of the head (5, 6) form a fork suitable for receiving the triangular area of the complementary head (6, 5) in order to form a hinge.

The vertical extension (20), the radial extension (22) and the triangular area can be manufactured integrally by molding a single part forming a molded arm made of filled polymer.

It is also possible to manufacture the arm by assembling three separate parts, namely a radial extension made up of a ring with a thickness corresponding to that of the triangular area, and a radial extension made up of a rectangular part having two recesses for passing the axis of the eyelet and the main roller. In this case, the axes also provide the assembly of the three parts that make up the head.

Optionally, at least one of the handles (7, 8) of any one of the embodiments (and preferably the lower arm) has markings (24) that can inform the user of the angle of curvature achieved. The reading is made at the intersection of the two arms. The visible marking at the intersection provides an indication of the level of curvature achieved. The value of each of the gradings is determined by a geometric calculation taking into account the dimensions of the arm, the rollers and the eyelets. The value can also be determined in an empirical manner, by performing consecutive bending operations of the rod in which the radius of curvature is measured after releasing the force, and noting the point of intersection at the time of maximum force, in order to allocate to same the value of the radius of curvature observed.

The invention claimed is:

1. A bending machine with a cam made up of two articulated arms, comprising:
a main roller that is coaxial with an axis of articulation of said arms, an end of a short portion of each one of said arms having means for exerting a bending force on a rod, wherein said means are made up of eyelets, each one of said eyelets being mounted on an end of the short portion of each one of said arms in a rotatably mobile manner about an axis of rotation of the eyelet, the axis of rotation of the eyelet being parallel to an axis of said main roller, wherein each eyelet comprises an opening with an axis perpendicular to the axis of rotation of the eyelet, the opening being arranged such as to enable the passage of the rod to be bent.

2. The bending machine according to claim 1, wherein each eyelet is made up of a cylindrical part, the cylindrical part having an end, the cylindrical part comprising a head located at the end of the cylindrical part, the head having an opening passing through the head, said part being mounted freely rotatable through a bore made in the end of the short portion of said arms.

3. The bending machine according to claim 1, wherein each arm extends respectively in a plane perpendicular to the axis of articulation of said arms.

4. The bending machine according to claim 3, wherein the eyelet mounted on a lower arm has a base with a thickness matching a thickness of an upper arm, so that centers of the openings of the two eyelets are coplanar.

5. The bending machine according to claim 1, wherein the two arms are flat, and are arranged parallel to a median plane.

6. The bending machine according to claim 1, wherein an angle formed between a straight line passing between the axis of rotation of one of the eyelets, and an axis of rotation of the main roller, and an axis passing between the axis of rotation of a main roller and a gripping area of a corresponding arm, comprises between 75° and 100°.

7. The bending machine according to claim 1, wherein an angle formed between a straight line passing between the axis of rotation of one of the eyelets and an axis of rotation of the main roller, and an axis passing between an axis of rotation of a main roller and a gripping area of a corresponding arm, is 90°.

8. The bending machine according to claim 1, wherein each arm comprises rear portion configured as a handle, the rear portion being connected to the short portion provided with the eyelet by an front portion, said handle forming a divergent angle with said front portion.

9. The bending machine according to claim 1, wherein the main roller has a groove with a radius substantially equal to that of the rod to be bent, a center of which is coplanar with a center of the openings formed in the eyelets.

10. The bending machine according to claim 1, wherein the arms are configured to allow a crossing of intermediate areas thereof.

11. The bending machine according to claim 1, wherein the short portion of each arm comprises a triangular shape that supports a vertical extension, coaxial with said axis of rotation of the eyelet, with a height matching the thickness of the short portion of a complementary arm, said vertical extension including a radial extension, extending parallel to the short portion, between the axis of rotation of the eyelet and the axis of rotation of the main roller in order to form, with the vertical extension and the short portion a fork suitable for receiving the triangular shaped short portion of the complementary arm so as to form a hinge.

12. The bending machine according to claim 1, wherein a vertical extension, a radial extension and a head are formed integrally by moulding a single part.

13. The bending machine according to claim 1, wherein said short portion has a triangular shape extending away from the axis of articulation.

14. The bending machine according to claim 1, wherein at least one handle has markings that represent a radius of curvature achieved.

15. The bending machine according to claim 1, wherein the arms comprise a polymer.

16. The bending machine according to claim 1, wherein each eyelet is arranged relative to the main roller configured to allow the passage of the rod therebetween.

17. The bending machine according to claim 1, wherein, each eyelet has an outer perimeter constituting a bearing area for the rod.

18. The bending machine according to claim 17, wherein the outer perimeter comprises one planar bearing zone and one circular bearing zone.

* * * * *